US006433027B1

(12) United States Patent
Bozung et al.

(10) Patent No.: US 6,433,027 B1
(45) Date of Patent: *Aug. 13, 2002

(54) MEDICAMENT COMPOSITIONS BASED ON TIOTROPIUM BROMIDE AND FORMOTEROL FUMARATE

(75) Inventors: Karl-Heinz Bozung, Mainz; Michel Pairet, Stromberg; Richard Reichl, Gau-Aglesheim; Alexander Walland, Ingelheim am Rhein, all of (DE)

(73) Assignee: Boehringer Ingelheim Pharma KG, Ingelheim (DE)

(*) Notice: Subject to any disclaimer, the term of this patent is extended or adjusted under 35 U.S.C. 154(b) by 11 days.

This patent is subject to a terminal disclaimer.

(21) Appl. No.: 09/695,581

(22) Filed: Oct. 24, 2000

Related U.S. Application Data

(63) Continuation of application No. 09/568,880, filed on May 9, 2000.

(30) Foreign Application Priority Data

May 12, 1999 (DE) .......................... 199 21 693

(51) Int. Cl.[7] .......................... A61P 11/06; A61P 11/08; A61K 31/14; A61K 31/537; A61K 31/167
(52) U.S. Cl. .................... 514/826; 514/229.5; 514/642; 514/629; 424/43
(58) Field of Search .................... 514/672, 826, 514/424, 704, 643, 629, 229.5; 424/43

(56) References Cited

U.S. PATENT DOCUMENTS 5,290,539 A * 3/1994 Marecki ........................ 424/45
5,676,930 A * 10/1997 Jager et al. .................... 424/45

FOREIGN PATENT DOCUMENTS

| EP | 0 504 112 A2 | 3/1992 |
|----|---|---|
| WO | WO 87/07502 A1 | 12/1987 |
| WO | WO95/24889 A1 | 9/1995 |
| WO | WO96/19968 A1 | 7/1996 |
| WO | WO97/34871 A1 | 9/1997 |
| WO | WO99/51205 A1 | 10/1999 |
| WO | WO00/47200 A1 | 8/2000 |

OTHER PUBLICATIONS

U. S. application No. 09/416,476, Hochrainer et al., filed Oct. 12, 1999.
Bower, C.; Fractal morphology of drug aggregates in aerosol propellant suspensions;International Journal of Pharmaceutics; 1995; 229–235; V. 118.
Barnes, C.; Chronic obstructive pulmonary disease: new opportunities for drug development; Trends in Pharma. Sci., 1998; 415–423; V. 19.
Rees, P.J.; Bronchodilators in the therapy of chronic obstructive pulmonary disease; Eur. Respir. Mon. 3/7; 1998; 135–149.
Banholzer, Ralf et al; "Crystalline Tiotropium Bromide Monohydrate, Processes for the Preparation thereof, and Pharmaceutical Compositions"; U.S.S.N. 09/961,822; Filed Sep. 24, 2001; Attorney Docket No. 1/1148.

* cited by examiner

Primary Examiner—Edward J. Webman
Assistant Examiner—Helen Nguyen
(74) Attorney, Agent, or Firm—Robert P. Raymond; Timothy X. Witkowski

(57) ABSTRACT

The present invention relates to new medicament compositions based on anticholinergic compounds, which have a long-lasting effect, and β-mimetics, which have a long-lasting effect, processes for their production and their use in the therapy of respiratory ailments.

5 Claims, 1 Drawing Sheet

MEDICAMENT COMPOSITIONS BASED ON TIOTROPIUM BROMIDE AND FORMOTEROL FUMARATE

RELATED APPLICATION

This application is a continuation of U.S. Ser. No. 09/568,880, filed May 9,2000.

FIELD OF THE INVENTION

The present invention relates to new medicament compositions based on anticholinergic compounds, which have a long-lasting effect, and β-mimetics, which have a long-lasting effect, processes for their production and their use in the therapy of respiratory ailments such as asthma or chronic obstructive pulmonary disease (COPD).

BACKGROUND OF THE INVENTION

It is known from the prior art that β-mimetics and anticholinergics can successfully be used as bronchospasmolytics for the treatment of obstructive respiratory ailments, such as, e.g., asthma. Substances with β-sympatho-mimetic effectiveness, such as, e.g., the active substance formoterol, also known from the prior art, can, however, be associated with undesirable side-effects when administered to humans.

Generally, the central effects manifest as unease, excitation, sleeplessness, fear, shaking fingers, outbreaks of sweating and headaches. Here, inhalative application does not exclude these side-effects although they are generally less severe than with peroral or parenteral application.

The side-effects of the β-sympatho-mimetics used as asthma agents are primarily associated with a more or less pronounced β1-stimulating effect on the heart. It generates tachycardia, palpitation, angina pectoris-like complaints and arrhythmia [P. T. Ammon (Ed.), Medicament Side-effects and Interactions, *Wissenschaftliche Verlagsgesellschaft*, Stuttgart 1986, S. 584].

DESCRIPTION OF THE INVENTION

Surprisingly, it has now been found that the above-mentioned sidefects can be substantially reduced by a combination of a β-sympatho-mimetic, which has a long-lasting effect, with an anticholinergic, which has a long-lasting effect.

In addition, it was also very surprisingly discovered that the bronchospasmolytic effects of the anticholinergic, which has a long-lasting effect, and the β-mimetic, which has a long-lasting effect, increase in a superadditive manner.

Hence with the combination of active ingredients according to the invention, a substantial increase in effectiveness can be expected—in comparison to the individual substances and combinations known from the prior art—in the case of both COPD and asthma.

The following active ingredients can preferably be used as β-mimetics, which have a long-lasting effect, in the active ingredients combination according to the invention: bambuterol, bitolterol, carbuterol, clenbuterol, fenoterol, formoterol, hexoprenalin, ibuterol, pirbuterol, procaterol, reproterol, salmeterol, sulfonterol, terbutalin, tolubuterol, 4-hydroxy-7-[2-{[2-{[3-(2-phenylethoxy)propyl]sulfonyl}ethyl]-amino}ethyl]-2(3H-benzothiazolone, 1-(2-fluoro4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol or 1-(4-ethoxycarbonylamino-3-cyano-5-fluorophenyl)-2-(tert-butylamino)ethanol, optionally in the form of their racemates, their enantiomers, their diastereomers, and mixtures thereof, and optionally their pharmacologically-compatible acid addition salts.

The following are preferably used as β-mimetics, which have a long-lasting effect, in the active ingredients combination according to the invention: formoterol, salmeterol, 4-hydroxy-7-[2-{[2-{[3-(2-phenylethoxy)propyl]sulfonyl}ethyl]-amino}ethyl]-2(3H)-benzothiazolone, 1-(2-fluoro4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol or 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers and mixtures thereof, and optionally their pharmacologically-compatible acid addition salts.

Especially preferably, the following are used as β-mimetics in the medicament compositions according to the invention: formoterol or salmeterol, optionally in the form of their racemates, their enantiomers, their diastereomers and mixtures thereof, and optionally their phaimacologically-compatible acid addition salts.

As stated above, the β-mimetics which have a long-lasting effect can be converted and used in the form of their physiologically and pharmacologically-compatible salts. The following can be considered, by way of example, to represent the acid addition salts: hydrochloric acid, hydrobromic acid, sulphuric acid, phosphoric acid, methanosulphonic acid, acetic acid, fumaric acid, succinic acid, lactic acid, citric acid or maleic acid. Furthermore, mixtures of the aforementioned acids can be used.

From the viewpoint of the superadditive bronchospasmolytic effect, the fumarate of formoterol (abbreviated to formoterol FU) is especially preferred as a β-mimetic which has a long-lasting effect. Here, the active substance formoterol can be used as an enantiomer or diastereomer mixture or in the form of the individual enantiomers/diastereomers. With the same preferred significance, according to the invention, salmeterol can also be used as a β-mimetic which has a long-lasting effect, optionally in the form of its racemates, enantiomers, of which the (R) enantiomer is most especially preferred, and optionally its pharmacologically-acceptable addition salts.

As anticholinergics which have a long-lasting effect, basically those which are already known from the prior art, such as glycopyrronium bromide and esters of bi- and tricyclic amino alcohols, are suitable, such as are known from European disclosure document 0 418 716 and International Patent Application WO 92/16528, and to the full contents of which reference is hereby made.

Within the framework of the invention, glycopyrronium-bromide can especially be considered as an anticholinergic which has a long-lasting effect, and compounds of formula (I)

$$Z\overset{O}{\underset{}{\|}}C-O-A \qquad (I)$$

can be considered as esters of bi- and tricyclic amino alcohols wherein

A denotes a group of general formula (II)

$$-CH\underset{CH_2-CH}{\overset{CH_2-CH}{<}}{}^+NRR'\underset{}{>}Q, \qquad (II)$$

in which

Q denotes one of the double-bonded groups —CH$_2$—CH$_2$—, —CH$_2$—CH$_2$—CH$_2$—, —CH=CH—, or $$-CH\underset{O}{\overset{}{\diagdown\diagup}}CH-;$$

R denotes an optionally halogen- or hydroxy-substituted $C_1$–$C_4$ alkyl group, R' denotes a $C_1$–$C_4$ alkyl group and R and R' can also combine to form a $C_4$–$C_6$ alkylene group, and an equivalent of an anion X is counters the positive charge of the N atom, Z denotes one of the groups $$R^2\underset{R^3}{\overset{R^1}{-}}C- \quad \text{or} \qquad (III)$$

(IV)

wherein

Y represents a single bond, an O or S atom or one of the groups —CH$_2$—, —CH$_2$—CH$_2$—, —CH=CH—, —OCH$_2$— or —SCH$_2$—;

R$^1$ denotes hydrogen, OH, $C_1$–$C_4$ alkoxy or $C_1$–$C_4$ alkyl, which can optionally be substituted by hydroxy;

R$^2$ denotes a thienyl, phenyl, furyl, cyclopentyl or cyclohexyl group, wherein these groups can also be substituted by methyl, and thienyl and phenyl can also be substituted by fluorine or chlorine, R$^3$ denotes hydrogen or a thienyl or phenyl group, which can optionally be substituted by halogen or $C_1$–$C_4$ alkyl, optionally in the form of their racemates, their enantiomers, their diastereomers and mixtures thereof.

Within the framework of the invention, glycopyrronium-bromide can especially preferably be considered as an anticholinergic which has a long-lasting effect, and compounds of formula (I) can be considered as esters of bi- and tricyclic amino alcohols, wherein A denotes a group of general formula (II)

$$-CH\underset{CH_2-CH}{\overset{CH_2-CH}{<}}{}^+NRR'\underset{}{>}Q, \qquad (II)$$

in which

Q denotes one of the double-bonded groups —CH=CH—, —CH$_2$—CH$_2$— or $$-CH\underset{O}{\overset{}{\diagdown\diagup}}CH-;$$

R denotes a methyl, ethyl or propyl group, optionally substituted by fluorine or hydroxy, R' denotes methyl, ethyl or propyl, preferably methyl, and an equivalent of an anion X selected from the group comprising chloride, bromide and methanesulphonate, preferably bromide, counters the positive charge of the N atom, Z denotes one of the groups $$R^2\underset{R^3}{\overset{R^1}{-}}C- \quad \text{or} \qquad (III)$$

(IV)

wherein

Y represents a single bond or an O atom;

R$^1$ denotes hydrogen, OH, methoxy, ethoxy, propoxy, methyl, ethyl, propyl, hydroxymethyl, hydroxyethyl, or hydroxypropyl;

R$^2$ denotes a thienyl, phenyl, or cyclohexyl group, wherein these groups can also be substituted by methyl, and thienyl and phenyl can also be substituted by fluorine or chlorine, R$^3$ denotes hydrogen, or a thienyl or phenyl group which can optionally be substituted by fluorine, chlorine or methyl, optionally in the form of their racemates, their enantiomers, their diastereomers and mixtures thereof.

According to the invention, medicament compositions in which compounds of formula (I) are used as anticholinergics which have a long-lasting effect are of special significance, wherein A denotes a group of general formula (II)

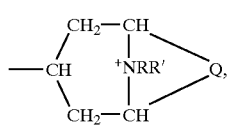
(II)

in which
Q denotes one of the double-bonded groups
—CH=CH—, —CH$_2$—CH$_2$— or

R denotes methyl or ethyl;
R' denotes methyl; and
an equivalent of the anion X= bromide is positioned opposite the positive charge of the N atom,
Z denotes one of the groups

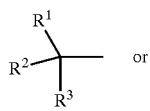
(III)

or

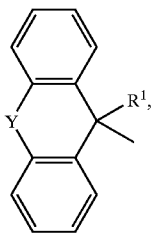
(IV)

wherein
Y denotes an O atom;
R$^1$ denotes hydrogen, OH or hydroxymethyl;
R$^2$ denotes a thienyl, phenyl or cyclohexyl group; and
R$^3$ denotes hydrogen, thienyl or phenyl group,
optionally in the form of their racemates, their enantiomers, their diastereomers and mixtures thereof.

Of the compounds named above, within the framework of the present invention those of the 3-α position are especially preferred.

The described anticholinergic active substances can optionally be used in the form of their pure enantiomers, mixtures thereof or their racemates.

It is especially preferred that tiotropium salt, especially tiotropium bromide [(1α,2β,4β,5α,7β)-7-[(hydroxy-2-thienylacetyl)oxy]-9,9-dimethyl-3-oxa-9-azoniatricyclo [3.3.1.0$^{2,4}$]nonane bromide monohydrate (abbreviated to tiotropium BR)] is used as an anticholinergic.

As alkyl groups (even insofar as they are components of other groups), unless otherwise defined, branched and unbranched alkyl groups with 1 to 4 carbon atoms are considered. By way of example, methyl, ethyl, propyl or butyl are named. Insofar as not otherwise named, all of the possible isomeric forms of the hereinbefore-named designations propyl and butyl are included. For example, the designation propyl includes the two isomeric groups n-propyl and isopropyl, the designation butyl, n-butyl, isobutyl, sec-butyl and tert-butyl. Optionally, common abbreviations are used to designate the hereinbefore-named alkyl groups, such as Me for methyl, Et for ethyl, etc.

As alkoxy groups (even insofar as they are components of other groups), unless otherwise defined, branched and unbranched alkyl groups, bridged via an oxygen atom and with 1 to 4 carbon atoms, are considered. The following are named by way of example: methoxy, ethoxy, propoxy (=propyloxy) or butoxy (=butyloxy). Here too, insofar as not otherwise named, all of the possible isomeric forms of the hereinbefore-named designations propoxy and butoxy are included.

Branched and unbranched alkylene bridges with 4 to 6 carbon atoms are considered as alkylene groups. The following are named by way of example: butylene, pentylene, and hexylene. Insofar as not otherwise named, all of the possible isomeric forms of the hereinbefore-named designations butylene, pentylene, hexylene are included. For example, the designation butylene includes the isomers n-butylene, 1-methylpropylene, 2-methylpropylene, 1,1-dimethylethylene, 1,2-dimethylethylene, etc.

Generally, fluorine, chlorine, bromine, or iodine are designated as halogen.

Insofar as not otherwise mentioned, anion X is generally designated as fluorine, chlorine, bromine, iodine, methanesulphonate, fumarate, or citrate.

The active substance compositions according to the invention are preferably administered in the form of a dosing aerosol, however, any other form or parenteral or oral application is possible. Here, the application of dosing aerosols embodies the preferred application form, especially in the therapy of obstructive lung diseases or for the treatment of asthma.

Apart from applications in aerosols which operate via propellant gases, the active substance combinations according to the invention can also be administered by means of so-called atonisers, via which solutions of pharmacologically-active substances can be sprayed under high pressure so that a mist of inhalable particles results. The advantage of these atomisers is that the use of propellant gases can be completely dispensed with.

The medicaments intended for inhalation are usually dissolved in an aqueous or ethanolic solution, wherein solvent mixtures of ethanol or water are also suitable, depending on the solution characteristics of the active substances.

Such atomisers are described, for example, in PCT Patent Application No. WO91/14468 and International Patent Application PCT/EP96/04351, reference here being made to the contents thereof. With the atomisers described here, which are also known under the designation Respimat®, defined volumes of solutions containing active substances are sprayed at high pressure through small jets so that inhalable aerosols result with a preferred particle size of between 1 and 10, preferably between 2 and 5 micrometres.

Amongst others, mixtures which, e.g., contain ethanol as a solvent are suitable for use as solvents for medicament preparation.

Apart from water, other components of the solvent are optionally other co-solvents and the medicament preparation can also contain flavorings and other pharmacological adjuvants. Examples of co-solvents are those which contain hydroxyl groups or other polar groups such as alcohols—especially isopropyl alcohol, glycols—especially propylene glycol, polyethylene glycol, polypropylene glycol, glycol ether, glycerol, polyoxyethylene alcohols and esters of polyoxyethylene fatty acids. Co-solvents are suited to increasing the solubility of adjuvants and, optionally, the active substance. Other pharmacological adjuvants can be added, such as, e.g., preservatives, especially benzalkonium chloride.

The preferred quantity of preservatives, especially benzalkonium chloride, is between 8 and 12 mg/100 ml solution.

Complex formers can be added to the active substance combination to avoid spray anomalies. Suitable complex formers are those which are pharmacologically-acceptable, especially those which are already permitted under drug licensing laws. EDTA, nitrilotriacetic acid, citric acid and ascorbic acid, and also their salts, are especially suitable. The disodium salt of ethylenediamtetraacetic acid is especially suitable.

The proportion of dissolved active substance composition in the finished medicament preparation is between 0.001 and 5%, preferably between 0.005 and 3%, and especially 0.01 to 2%. The maximum concentration of medicament is dependent on solubility in solvent and the necessary dosage for attaining the desired therapeutic effect.

The following preparation forms are cited as a formulation example:

| Component Parts | Composition in mg/100 ml |
|---|---|
| Tiotropium bromide | 333.3 mg |
| Formoterol fumarate | 333.3 mg |
| Benzalkonium chloride | 10.0 mg |
| EDTA | 50.0 mg |
| HCl (1N) | ad pH 3.4 |
| Tiotropium bromide | 333.3 mg |
| Salmeterol xinafoate | 666.6 mg |
| Benzalkonium chloride | 10.0 mg |
| EDTA | 50.0 mg |
| HCl (1N) | ad pH 3.4 |

In addition, the active substance combinations can also be inhaled in the form of a powder. The production of such administration forms is known from the prior art. Apart from the active substance combination, corresponding to the present invention, they contain pharmacologically-compatible carrier or adjuvant substances, such as, e.g., microcrystalline lactose. The dose provided for inhalation can, for example, be filled into capsules and has, e.g., the following composition:

| Component Parts | Quantity |
|---|---|
| Tiotropium bromide hydrate | 6 μg |
| Formoterol fumarate × 2 $H_2O$ | 6 μg |
| Lactose monohydrate | ad 25 mg |

Results of the Experiment

Bronchospasmolytic and cardiovascular effect of tiotropium bromide, formoterol fumarate and combinations thereof after inhalative application of an aqueous solution to narcotized dogs by means of Respimat®.

Material and Methods 18 mongrel dogs with a body weight of 27 to 32 kg. Kept in individual or communal cages, pelleted standard food, last fed approximately 15 hours before the start of the tests, drinking water freely available.

After pre-medication with 2 mg/kg morphine hydrochloride i.m., 30 mg/kg pentobarbital-sodium (Nembuta®) is slowly injected intravenously. The animals are relaxed with 1.0 mg/kg i.v. suxamethonium. After intubation via a servo ventilator 900C (Siemens), the animals are ventilated with ambient air and oxygen (4:1), frequency 15/min., breath volume 6–8 l/min. For registration of the breathing mechanics, breath flow is determined by means of a pressurizing pipe (flesh no. 1), installed directly before the orotracheal tube, of a differential pressure recorder and amplifier DCB-4C. A catheter is placed in the trachea and a second (balloon) catheter is placed in the lung section of the esophagus. Both are connected with a differential pressure recorder and amplifier for determination of the transpulmonary pressure. A breath mechanics computer (IFD-M ühlheim) determines the pulmonary resistance (R) from the registered pressure values. From this, a computer program VAS-1 LA (IFD-Mühlheim) calculates:

$$\text{Pulmonary resistance} = \frac{\text{max. transpulmonary pressure}}{\text{breath flow}}$$

Registration of heart frequency is via ECG (extremity derivative II) and cardiotachometer.

After an equilibration period of 30 minutes, short-term bronchospasms are generated by i.v. injection of 10 μg/kg acetylcholine chloride—this is repeated 2–3× within a 10-minute period. The test substances tiotropium bromide, formoterol fumarate and the combination of both substances are administered as aqueous solutions with the BINEB atomizer (Respimat®). Application of the combinations takes place with the individual combinations with an interval of approximately 1 minute. With the BINEB system, the triggering mechanism takes place at the end of the expiration phase and the atomized solution is pressed into the tracheobronchial tree in the following inspiration phase of the breath pump.

| Dosages | |
|---|---|
| Tiotropium bromide: | 3 and 10 μg/15 μl |
| Formoterol fumarate: | 3 and 10 μg/15 μl |
| Tiotropium bromide + formoterol fumarate: | 3 + 3 μg or<br>10 + 10 μg/15 μl |

Tables 1–6 show the starting values and the values after substance treatment over time within 180 minutes. The percentile inhibitions of the pulmonary resistance increases, induced by ACh, over the time from 180 minutes.

Results

The results are shown in the Tables and in the Diagrams. 3 and 10 μg tiotropium bromide, or formoterol firmarate, inhibit the bronchial resistance increased by intravenous hmjection of ACh, stepped with regard to dosage and clear. The maximum bronchospasmolytic effect of formoterol FU rapidly occurs with both dosages, that of tiotropium BR delayed after approximately 60 minutes. The effective duration of formoterol FU is comparatively short, especially with the low dosages, but according to expectations those of the tiotropium BR were continuous until the end of the test (180 minutes).

With the combination of 3 μg tiotropium bromide+3 μg formoterol FU, a very rapidly-occurring bronchiospasmolysis of 90% was attained which continued practically unchanged until the end of the test. The protective effect of the combination substantially exceeds that of the individual components, but also the sum of the individual effects of 3 μtiotropium bromide and 3 μg formoterol FU. It exceeds the effects of 10 μg tiotropium bromide or 10 μg formoterol fumarate (cf. Diagram 2).

Tiotropium bromide on its own has no influence at all on the heart frequency, either with 3 μg or 10 μg. On the other hand, formoterol FU increases it in stages, dependent on dosage, and above all by a maximnum of over 90% with high dosage. Values of over 80% are still measured after the end of the test. The frequency effects are substantially lessened with the combinations 3+3 μg, or also 10+10 μg tiotropium bromide and formoterol fiumarate, and lie below 30%.

Evaluation

Entirely surprising results were found with the combination of the anticholinergic and the β-mimetic as opposed to the individual substances:

1. Rapid onset of effect

2. Long duration of effect but primarily

3. The superadditive bronchospasmolytic effect, and

4. The substantially reduced frequency increase, especially with the high formnoterol dose.

A substantially-improved therapeutic effect can be expected with the combination preparation for both COPD and asthma, associated with the advantage of minimal cardial side-effects.

TABLE 1

Influence of 3 μg Tiotropium Bromide on the Heart Frequency of Narcotized Dogs After Inhalative Application via Respimat ®, n = 6

| | | | | Minutes after application | | | | | |
|---|---|---|---|---|---|---|---|---|---|
| | Control | 1 | 5 | 10 | 20 | 30 | 60 | 120 | 180 |
| Heart frequency (beats/min.) | | | | | | | | | |
| | 66.50 | 63.00 | 67.00 | 64.00 | 61.00 | 63.00 | 67.00 | 63.00 | 66.00 |
| | 87.50 | 87.00 | 84.00 | 82.00 | 87.00 | 81.00 | 89.00 | 87.00 | 87.00 |
| | 86.50 | 84.00 | 84.00 | 89.00 | 89.00 | 89.00 | 84.00 | 77.00 | 86.00 |
| | 109.50 | 115.00 | 115.00 | 116.00 | 120.00 | 121.00 | 104.00 | 105.00 | 105.00 |
| | 110.50 | 119.00 | 119.00 | 118.00 | 110.00 | 110.00 | 111.00 | 110.00 | 100.00 |
| | 85.50 | 85.00 | 87.00 | 90.00 | 93.00 | 97.00 | 97.00 | 92.00 | 96.00 |
| Mean value | 91.00 | 92.17 | 92.67 | 93.17 | 93.33 | 93.50 | 92.00 | 89.00 | 90.00 |
| sem | 6.80 | 8.63 | 8.23 | 8.45 | 8.35 | 8.46 | 6.40 | 7.14 | 5.66 |
| 3 μg tiotropium bromide, % alteration | | | | | | | | | |
| | 66.50 | −5.26 | 0.75 | −3.76 | −8.27 | −5.26 | 0.75 | −5.26 | −0.75 |
| | 87.50 | −0.57 | −4.00 | −6.29 | −0.57 | −7.43 | 1.71 | −0.57 | −0.57 |
| | 86.50 | −2.89 | −2.89 | 2.89 | 2.89 | 2.89 | −2.89 | −10.98 | −0.58 |
| | 109.50 | 5.02 | 5.02 | 5.94 | 9.59 | 10.50 | −5.02 | −4.11 | −4.11 |
| | 110.50 | 7.69 | 7.69 | 6.79 | −0.45 | −0.45 | 0.45 | −0.45 | −9.50 |
| | 85.50 | −0.58 | 1.75 | 5.26 | 8.77 | 13.45 | 13.45 | 7.60 | 12.28 |
| Mean value | 91.00 | 0.57 | 1.39 | 1.81 | 1.99 | 2.28 | 1.41 | −2.30 | −0.54 |
| sem | 6.80 | 1.99 | 1.83 | 2.25 | 2.72 | 3.42 | 2.62 | 2.53 | 2.93 |

TABLE 2

Influence of 10 μg Tiotropium Bromide on the Heart Frequency of Narcotized Dogs After Inhalative Application via Respimat ®, n = 6

| | | | | Minutes after application | | | | | |
|---|---|---|---|---|---|---|---|---|---|
| | Control | 1 | 5 | 10 | 20 | 30 | 60 | 120 | 180 |
| Heart frequency (beats/min.) | | | | | | | | | |
| | 66.50 | 79.00 | 75.00 | 75.00 | 77.00 | 79.00 | 74.00 | 75.00 | 70.00 |
| | 87.50 | 96.00 | 91.00 | 88.00 | 89.00 | 90.00 | 85.00 | 83.00 | 83.00 |
| | 86.50 | 85.00 | 80.00 | 79.00 | 77.00 | 76.00 | 75.00 | 76.00 | 87.00 |
| | 109.50 | 104.00 | 102.00 | 101.00 | 101.00 | 101.00 | 103.00 | 103.00 | 105.00 |
| | 110.50 | 102.00 | 102.00 | 102.00 | 101.00 | 96.00 | 101.00 | 102.00 | 101.00 |
| | 85.50 | 76.00 | 75.00 | 76.00 | 77.00 | 74.00 | 73.00 | 74.00 | 74.00 |
| Mean value | 91.00 | 90.33 | 87.50 | 86.83 | 87.00 | 86.00 | 85.17 | 85.50 | 86.67 |
| sem | 6.80 | 4.89 | 5.17 | 5.00 | 4.82 | 4.60 | 5.61 | 5.53 | 5.75 |

TABLE 2-continued

Influence of 10 μg Tiotropium Bromide on the Heart Frequency of Narcotized Dogs After Inhalative Application via Respimat ®, n = 6

|  | Control | \multicolumn{8}{c|}{Minutes after application} |
|---|---|---|---|---|---|---|---|---|---|
|  |  | 1 | 5 | 10 | 20 | 30 | 60 | 120 | 180 |
| 10 μg tiotropium bromide, % alteration | | | | | | | | | |
|  | 66.50 | 18.80 | 12.78 | 12.78 | 15.79 | 18.80 | 11.28 | 12.78 | 5.26 |
|  | 87.50 | 9.71 | 4.00 | 0.57 | 1.71 | 2.86 | −2.86 | −5.14 | −5.14 |
|  | 86.50 | −1.73 | −7.51 | −8.67 | −10.98 | −12.14 | −13.29 | −12.14 | 0.58 |
|  | 109.50 | −5.02 | −6.85 | −7.76 | −7.76 | −7.76 | −5.94 | −5.94 | −4.11 |
|  | 110.50 | −7.69 | −7.69 | −7.69 | −8.60 | −13.12 | −8.60 | −7.69 | −8.60 |
|  | 85.50 | −11.11 | −12.28 | −11.11 | −9.94 | −13.45 | −14.62 | −13.45 | −13.45 |
| Mean value | 91.00 | 0.49 | −2.93 | −3.65 | −3.30 | −4.14 | −5.67 | −5.26 | −4.24 |
| sem | 6.80 | 4.68 | 3.84 | 3.66 | 4.25 | 5.23 | 3.84 | 3.86 | 2.70 |

TABLE 3

Influence of 3 μg Formoterol Fumarate on the Heart Frequency of Narcotized Dogs After Inhalative Application via Respimat ®, n = 6

|  | Control | \multicolumn{8}{c|}{Minutes after application} |
|---|---|---|---|---|---|---|---|---|---|
|  |  | 1 | 5 | 10 | 20 | 30 | 60 | 120 | 180 |
| Heart frequency (beats/min.) | | | | | | | | | |
|  | 94.50 | 102.00 | 105.00 | 129.00 | 134.00 | 138.00 | 134.00 | 115.00 | 108.00 |
|  | 133.00 | 123.00 | 140.00 | 162.00 | 165.00 | 159.00 | 153.00 | 147.00 | 140.00 |
|  | 60.00 | 67.00 | 64.00 | 100.00 | 95.00 | 89.00 | 86.00 | 88.00 | 86.00 |
|  | 80.50 | 91.00 | 95.00 | 110.00 | 100.00 | 95.00 | 94.00 | 94.00 | 96.00 |
|  | 106.50 | 129.00 | 137.00 | 138.00 | 141.00 | 145.00 | 140.00 | 130.00 | 130.00 |
|  | 92.50 | 107.00 | 116.00 | 125.00 | 126.00 | 128.00 | 128.00 | 120.00 | 120.00 |
| Mean value | 94.50 | 103.17 | 109.50 | 127.33 | 126.83 | 125.67 | 122.50 | 115.67 | 113.33 |
| sem | 10.03 | 9.19 | 11.59 | 8.89 | 10.71 | 11.44 | 10.87 | 9.02 | 8.39 |
| 3 μg formoterol fumarate, % alteration | | | | | | | | | |
|  | 94.50 | 7.94 | 11.11 | 36.51 | 41.80 | 46.03 | 41.80 | 21.69 | 14.29 |
|  | 133.00 | −7.52 | 5.26 | 21.80 | 24.06 | 19.55 | 15.04 | 10.53 | 5.26 |
|  | 60.00 | 11.67 | 6.67 | 66.67 | 54.33 | 48.33 | 43.33 | 46.67 | 43.33 |
|  | 80.50 | 13.04 | 18.01 | 36.65 | 24.44 | 18.01 | 16.77 | 16.77 | 19.25 |
|  | 106.50 | 21.13 | 28.64 | 29.58 | 32.39 | 36.15 | 31.46 | 22.07 | 22.07 |
|  | 92.50 | 15.68 | 25.41 | 35.14 | 36.22 | 38.38 | 38.38 | 29.73 | 29.73 |
| Mean value | 94.50 | 10.32 | 15.85 | 37.72 | 36.17 | 34.41 | 31.13 | 24.58 | 22.32 |
| sem | 10.03 | 3.99 | 3.99 | 6.24 | 5.25 | 5.28 | 5.10 | 5.12 | 5.36 |

TABLE 4

Influence of 10 μg Formoterol Fumarate on the Heart Frequency of Narcotized Dogs After Inhalative Application via Respimat ®, n = 6

|  | Control | \multicolumn{8}{c|}{Minutes after application} |
|---|---|---|---|---|---|---|---|---|---|
|  |  | 1 | 5 | 10 | 20 | 30 | 60 | 120 | 180 |
| Heart frequency (beats/min.) | | | | | | | | | |
|  | 94.50 | 116.00 | 153.00 | 155.00 | 157.00 | 159.00 | 163.00 | 176.00 | 152.00 |
|  | 133.00 | 145.00 | 136.00 | 191.00 | 204.00 | 207.00 | 210.00 | 209.00 | 205.00 |
|  | 60.00 | 109.00 | 146.00 | 152.00 | 153.00 | 150.00 | 149.00 | 146.00 | 141.00 |

TABLE 4-continued

Influence of 10 μg Formoterol Fumarate on the Heart Frequency of
Narcotized Dogs After Inhalative Application via Respimat ®, n = 6

| | Control | \multicolumn{8}{c}{Minutes after application} |
| | | 1 | 5 | 10 | 20 | 30 | 60 | 120 | 180 |
|---|---|---|---|---|---|---|---|---|---|
| | 80.50 | 96.00 | 120.00 | 144.00 | 156.00 | 156.00 | 140.00 | 140.00 | 130.00 |
| | 106.50 | 105.00 | 120.00 | 160.00 | 158.00 | 150.00 | 150.00 | 145.00 | 145.00 |
| | 92.50 | 122.00 | 122.00 | 130.00 | 135.00 | 140.00 | 140.00 | 135.00 | 135.00 |
| Mean value | 94.50 | 115.50 | 132.83 | 155.33 | 160.50 | 160.33 | 158.67 | 158.50 | 151.33 |
| sem | 10.03 | 6.94 | 5.88 | 8.32 | 9.38 | 9.70 | 10.83 | 11.68 | 11.18 |
| 10 μg formoterol fumarate, % alteration | | | | | | | | | |
| | 94.50 | 22.75 | 61.90 | 64.02 | 66.14 | 68.25 | 72.49 | 86.24 | 60.85 |
| | 133.00 | 9.02 | 2.26 | 43.61 | 53.38 | 55.64 | 57.89 | 57.14 | 54.14 |
| | 60.00 | 81.67 | 143.33 | 153.33 | 155.00 | 150.00 | 148.33 | 143.33 | 135.00 |
| | 80.50 | 19.25 | 49.07 | 78.88 | 93.79 | 93.79 | 73.91 | 73.91 | 61.49 |
| | 106.50 | −1.41 | 12.68 | 50.23 | 48.36 | 40.85 | 40.85 | 36.15 | 36.15 |
| | 92.50 | 31.89 | 31.89 | 40.54 | 45.95 | 51.35 | 51.35 | 45.95 | 45.95 |
| Mean value | 94.50 | 27.20 | 50.19 | 71.77 | 77.10 | 76.65 | 74.14 | 73.79 | 65.59 |
| sem | 10.03 | 11.86 | 20.70 | 17.32 | 17.15 | 16.44 | 15.70 | 15.77 | 14.42 |

TABLE 5

Influence of the Combination of 3 μg Tiotropium
Bromide + 3 μg Formoterol FU on the Heart Frequency
of Narcotized Dogs After Inhalative Application via Respimat ®, n = 6

| | Control | \multicolumn{8}{c}{Minutes after application} |
| | | 1 | 5 | 10 | 20 | 30 | 60 | 120 | 180 |
|---|---|---|---|---|---|---|---|---|---|
| Heart frequency (beats/min.) | | | | | | | | | |
| | 107.50 | 107.00 | 110.00 | 112.00 | 110.00 | 110.00 | 110.00 | 106.00 | 106.00 |
| | 143.00 | 153.00 | 162.00 | 160.00 | 158.00 | 154.00 | 161.00 | 146.00 | 145.00 |
| | 95.00 | 106.00 | 109.00 | 111.00 | 121.00 | 119.00 | 108.00 | 114.00 | 107.00 |
| | 95.50 | 110.00 | 117.00 | 129.00 | 128.00 | 130.00 | 129.00 | 123.00 | 123.00 |
| | 112.00 | 127.00 | 120.00 | 115.00 | 115.00 | 104.00 | 112.00 | 107.00 | 96.00 |
| | 101.50 | 100.00 | 110.00 | 110.00 | 112.00 | 114.00 | 110.00 | 101.00 | 95.00 |
| Mean value | 109.08 | 117.17 | 121.33 | 122.83 | 124.00 | 121.83 | 121.67 | 116.17 | 112.00 |
| sem | 7.31 | 8.07 | 8.33 | 7.69 | 7.31 | 7.37 | 8.47 | 6.73 | 7.78 |
| 3 μg tiotropium bromide + 3 μg formoterol fumarate, % alteration | | | | | | | | | |
| | 107.50 | −0.47 | 2.33 | 4.19 | 2.33 | 2.33 | 2.33 | −1.40 | −1.40 |
| | 143.00 | 6.99 | 13.29 | 11.89 | 10.49 | 7.69 | 12.59 | 2.10 | 1.40 |
| | 95.00 | 11.58 | 14.74 | 16.84 | 27.37 | 25.26 | 13.68 | 20.00 | 12.63 |
| | 95.50 | 15.18 | 22.51 | 35.08 | 34.03 | 36.13 | 35.08 | 28.80 | 28.80 |
| | 112.00 | 13.39 | 7.14 | 2.68 | 2.68 | −7.14 | 0.00 | −4.46 | −14.29 |
| | 101.50 | −1.48 | 8.37 | 8.37 | 10.34 | 12.32 | 8.37 | −0.49 | −6.40 |
| Mean value | 109.08 | 7.53 | 11.40 | 13.17 | 14.54 | 12.76 | 12.01 | 7.42 | 3.46 |
| sem | 7.31 | 2.91 | 2.87 | 4.86 | 5.38 | 6.41 | 5.12 | 5.55 | 6.23 |

TABLE 6

Influence of the Combination of 10 μg Tiotropium Bromide + 10 μg Formoterol Fumarate on the Heart Frequency of Narcotized Dogs After Inhalative Application via Respimat ®, n = 4

| | | Minutes after application | | | | | | | |
|---|---|---|---|---|---|---|---|---|---|
| | Control | 1 | 5 | 10 | 20 | 30 | 60 | 120 | 180 |

Heart frequency (beats/min.)

| | | | | | | | | | |
|---|---|---|---|---|---|---|---|---|---|
| | 107.50 | 107.00 | 107.00 | 114.00 | 117.00 | 117.00 | 117.00 | 116.00 | 119.00 |
| | 143.00 | 150.00 | 154.00 | 171.00 | 180.00 | 182.00 | 181.00 | 168.00 | 168.00 |
| | 95.00 | 107.00 | 107.00 | 116.00 | 124.00 | 127.00 | 125.00 | 122.00 | 126.00 |
| | 95.50 | 116.00 | 117.00 | 120.00 | 127.00 | 129.00 | 130.00 | 120.00 | 123.00 |
| Mean value | 110.25 | 120.00 | 121.25 | 130.25 | 137.00 | 138.75 | 138.25 | 131.50 | 134.00 |
| Sem | 11.29 | 10.22 | 11.17 | 13.64 | 14.49 | 14.65 | 14.50 | 12.23 | 11.42 |

10 μg tiotropium bromide + 10 μg formoterol fumarate, % alteration

| | | | | | | | | | |
|---|---|---|---|---|---|---|---|---|---|
| | 107.50 | −0.47 | −0.47 | 6.05 | 8.84 | 8.84 | 8.84 | 7.91 | 10.70 |
| | 143.00 | 4.90 | 7.69 | 19.58 | 25.87 | 27.27 | 26.57 | 17.48 | 17.48 |
| | 95.00 | 12.36 | 12.36 | 22.11 | 30.53 | 33.68 | 31.58 | 28.42 | 32.63 |
| | 95.50 | 21.47 | 22.51 | 25.65 | 32.98 | 35.08 | 36.13 | 25.65 | 28.80 |
| Mean value | 110.25 | 9.63 | 10.59 | 18.35 | 24.56 | 26.22 | 25.78 | 19.87 | 22.40 |
| sem | 11.29 | 4.77 | 4.80 | 4.29 | 5.44 | 6.04 | 5.97 | 4.61 | 5.06 |

Figure 1:
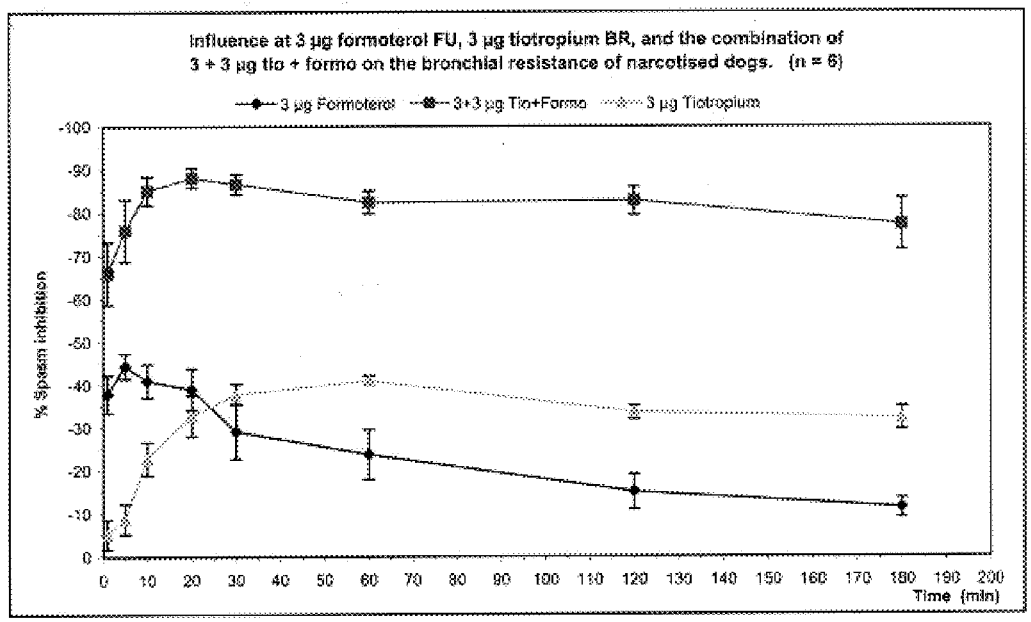
FIG. 1 shows the influence of 3 μg formoterol fumarate, 3 μg tiotropium bromide and a combination of 3 μg tiotropium bromide+3 μg formoterol fumarate on the bronchial resistance of narcotized dogs, n=6.
Figure 2:
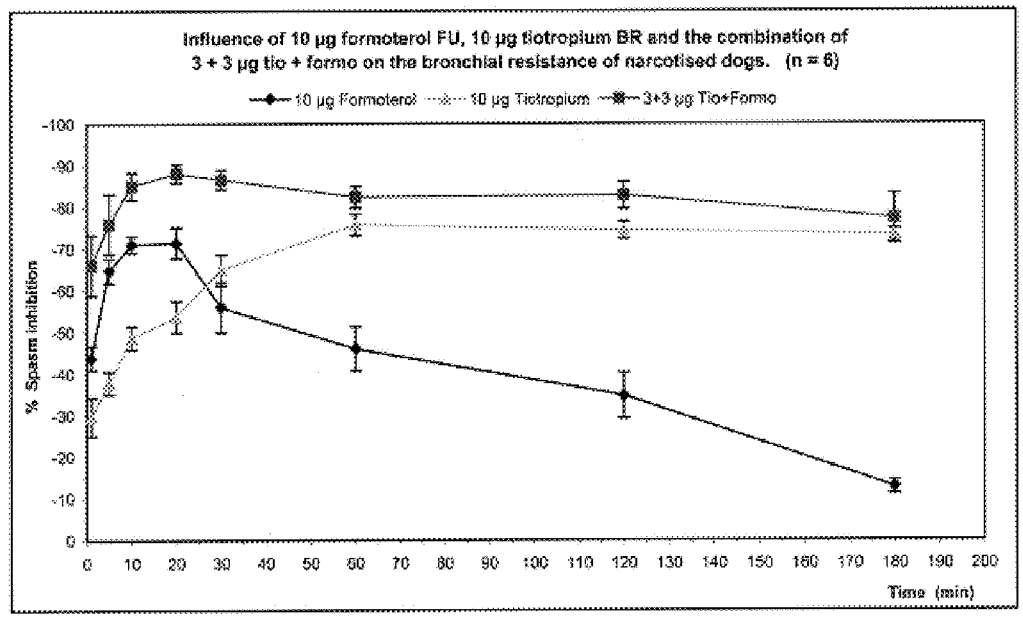
FIG. 2 shows the influence of 10 μg formoterol fumarate, 10 μg tiotropium bromide and a combination of 3 μg tiotropium bromide +3 μg formoterol fumarate on the bronchial resistance of narcotized dogs, n=6.

We claim:

1. A pharmaceutical composition comprising:
   (a) tiotropium bromide; and
   (b) formoterol fumarate.

2. The pharmaceutical composition according claim 1, wherein the pharmaceutical composition is inhaled.

3. A process for the production of a pharmaceutical composition according to claim 1, comprising:
   (a) mixing tiotropium bromide, and formoterol fumarate; and optionally
   (b) adding an adjuvant and/or carrier materials.

4. A method of treating respiratory ailments by administering to a host in need of such treatment a pharmaceutical composition according to claim 1.

5. The method according to claim 4, wherein the respiratory ailment is asthma or chronic obstructive pulmonary disease (COPD).

* * * * *

UNITED STATES PATENT AND TRADEMARK OFFICE
CERTIFICATE OF CORRECTION

PATENT NO. : 6,433,027 B1
DATED : August 13, 2002
INVENTOR(S) : Karl-Heinz Bozung, Michel Pairet, Richard Reichl and Alexander Walland It is certified that error appears in the above-identified patent and that said Letters Patent is hereby corrected as shown below:

Column 1,
Line 44, "sidefects" should read -- side-effects --.
Line 65, "fluoro4-" should read -- fluoro-4- --.

Column 2,
Line 24, "fluoro4-" should read -- fluoro-4- --.
Line 42, "phaimacologically" should read -- pharmacologically --.

Column 3,
Line 5, "glycopyrronium-" should read -- glycopyrronium --.

Column 6,
Line 34, "atonisers" should read -- atomisers --.

Column 8,
Line 51, "firmarate" should read -- fumarate --.
Line 53, "hmjection" should read -- injection --.

Column 9,
Line 6, "maximnum" should read -- maximum --.
Line 10, "fiumarate" should read -- fumarate --.

Column 10,
Line 11, "formnoterol" should read -- formoterol --.

Signed and Sealed this

Thirty-first Day of December, 2002

JAMES E. ROGAN
*Director of the United States Patent and Trademark Office*